United States Patent [19]

Schmid et al.

[11] Patent Number: 4,587,976

[45] Date of Patent: May 13, 1986

[54] METHOD OF, AND APPARATUS FOR, DETERMINING THE STARTING POINT AND THE END POINT OF CLOSED SIGNAL PATTERNS

[75] Inventors: Johann J. Schmid, Buchs; Werner Thie, Dielsdorf, both of Switzerland

[73] Assignee: Willi Studer AG, Fabrik für elektronische Apparate, Regensdorf, Switzerland

[21] Appl. No.: 693,683

[22] Filed: Jan. 22, 1985

[30] Foreign Application Priority Data

Jan. 25, 1984 [CH] Switzerland ............................ 327/84

[51] Int. Cl.$^4$ ............................................... A61B 5/04
[52] U.S. Cl. ..................................... 128/699; 364/417
[58] Field of Search ......................... 128/699; 364/417

[56] References Cited

U.S. PATENT DOCUMENTS

| 3,884,221 | 5/1975 | Eastman | 128/699 |
| 4,085,407 | 4/1978 | Stratbucker et al. | 128/699 |
| 4,136,690 | 1/1979 | Anderson et al. | 128/699 |

FOREIGN PATENT DOCUMENTS

| 0052512 | 5/1982 | European Pat. Off. . |
| 0086429 | 8/1983 | European Pat. Off. . |

OTHER PUBLICATIONS

Publication in "Biomedizinische Technik", vol. 23, No. 1/2, Jan. 1978, by R. D. Böckmann et al, entitled New Measuring Algorithms for Determining the QRS Start and End in Children Electrocardiograms and Children Vectorcardiograms.

Publication in "Medical and Biological Engineering and Computing", vol. 18, No. 3, pp. 303 to 311, May 1980, by I. C. Chien et al, entitled Computer Methods for Analyzing the High-Frequency Electrocardiogram, see Recording Methods; Analysis Techniques.

"Compedium Elektromedizin, Grundlagen, Technik, Anwendungen", by J. Patsold, Siemens, Berlin, pp. 26 to 30, see The EKG and its Interpretation.

"Computer", vol. 18, No. 7, pp. 42 to 45, Jul. 1975, M. L. Simoons et al: On-Line Analysis of Exercise Electrocardiograms.

"Wescon Technical Papers", vol. 19, Western Electronic Show and Convention, Sep. 16-19, 1975, R. V. Ramaswami: The Microcomputer in Diagnostic Health Care and Patient Monitoring.

Publication in IEEE Transactions on Biomedical Engineering, vol. BME-32, No. 1, Jan. 1985, pp. 43 to 50, by Hung T. Le et al, entitled Automated Analysis of Rodent Three-Channel Electrocardiograms and Vectorcardiograms.

*Primary Examiner*—William E. Kamm
*Attorney, Agent, or Firm*—Werner W. Kleeman

[57] ABSTRACT

When measuring signals are detected from a living being by means of electrodes, the moments of time associated with the starting point and the end point of the measuring signal are not unambiguously defined. In order to determine the starting point and the end point, a predetermined period of time of a selected signal pattern is subdivided into a first time interval and into a second time interval. The minimum distance between measuring points within the first time interval, on the one hand, and measuring points within the second time interval, on the other hand, is determined. The moments of time at which the measuring point of the first time interval associated with the minimum distance and the measuring point of the second time interval associated with the minimum distance are detected, are considered to constitute the starting point and the end point, respectively.

33 Claims, 6 Drawing Figures

METHOD OF, AND APPARATUS FOR, DETERMINING THE STARTING POINT AND THE END POINT OF CLOSED SIGNAL PATTERNS

CROSS-REFERENCE TO RELATED APPLICATION

This application is related to the commonly assigned, copending U.S. Application Ser. No. 06/464,765, filed Feb. 7, 1983, and entitled "Method and Apparatus for Cardiogoneometry", the disclosure of which is incorporated herein by reference.

BACKGROUND OF THE INVENTION

The present invention relates to a new and improved method of, and apparatus for, determining the starting point and the end point of a spatial closed signal pattern in a time sequence of individual ones of such spatial closed signal patterns, each of which is constituted by a series of measuring signals.

Spatial closed signal patterns of the aforementioned type may constitute, for example, physiological measuring signals which are picked up from a living being by means of electrodes and such spatial closed signal patterns occur, for example, in the as-such known methods of vector cardiography. Such a method is described in detail in European Patent Publication No. 0,086,429 and the aforementioned cognate U.S. Application Ser. No. 06/464,765. In this method as well as in other known methods of vector cardiography the starting points and the end points, for example, of the P-, QRS- and T-loops or waves are visually determined by the physician who must interpret the curves presented to him or her. This is evident, for example, from "Computers in Cardiology", 1982, IEEE, page 429 et seq. entitled "Automated Vector Cardiographic Analysis by an Inexpensive Microprocessor" (ISBN No. 0-8186-0024-1). It also follows therefrom that the determination of the starting points and of the end points by computation using an electronic computer tends to yield still less reliable results than the simple visual determination.

A further possibility for determining the starting point and the end point of a signal pattern as produced in the known vector cardiogram comprises the steps of selecting sections from a present signal pattern in which the signal does not or nearly does not change with time. An electrical starting, end, or base potential can be attributed to such sections which indicates that the starting point and the end point of the signal pattern are located in the region of such sections. However, when such a procedure is used, the definition of the starting point and of the end point is still indefinite with respect to time.

The determination of the starting point and the end point of a signal pattern is particularly difficult when the signal pattern has superimposed thereon oscillations of a very low frequency. In a vector cardiogram, for example, such an oscillation is effected by the breathing of the investigated person or patient. When the vector cardiogram is recorded under circulatory stress, such oscillations distort the signal pattern to such a degree that the determination of the starting point and the end point with sufficient reliability by means of the hitherto known methods is impossible.

SUMMARY OF THE INVENTION

Therefore, with the foregoing in mind it is a primary object of the present invention to provide a new and improved method of, and apparatus for, determining the starting point and the end point of a spatial closed signal pattern in a time sequence of individual ones of such spatial closed signal patterns, each of which is constituted by a series of measuring signals, in a manner which is not afflicted with the aforementioned drawbacks and limitations of the hitherto known methods.

Another important object of the present invention is directed to the provision of a new and improved method of, and apparatus for, determining the starting point and the end point of a spatial closed signal pattern in a time sequence of individual ones of such spatial closed signal patterns, each of which is constituted by a series of measuring signals, in such a manner that the moment of time associated with the starting point and the end point is unambiguously determined.

Now in order to implement these and still further objects of the invention, which will become more readily apparent as the description proceeds, the method of the present development is manifested by the features that, a predetermined number of electrodes is arranged in a predetermined configuration at a living being to be investigated and by means of these electrodes there is received the time sequence of individual ones of the spatial closed signal patterns. A predetermined period of time associated with a selected spatial closed signal pattern is subdivided into a first time interval and a second time interval and the spatial closed signal pattern is sampled. During this sampling operation there is determined, at each one of a predetermined number of sampling moments associated with said first time interval, the distance between selected ones of a predetermined number of sampling points associated with said predetermined number of sampling moments in said first time interval, on the one hand, and selected ones of a predetermined number of sampling points associated with a predetermined number of sampling moments associated with said second time interval, on the other hand. A minimum value of the distances between the predetermined sampling points associated with the first time interval and the predetermined sampling points associated with the second time interval is determined. The sampling point associated with the first time interval and the sampling point associated with the second time interval, between which the minimum distance exists, are respectively defined as the starting point and the end point of the selected individual spatial closed signal pattern.

As alluded to above, the present invention is not only concerned with the aforementioned method aspects, but also relates to a novel construction of an apparatus for recording a measured signal constituted by measured data which vary in time and space and define a time sequence of recurring individual closed signal patterns.

To achieve the aforementioned measures the inventive apparatus for recording a signal constituted by measured data which vary in time and space and define a time sequence of recurring individual closed signal patterns, in its more specific aspects comprises:

a measuring unit comprising a predetermined number of sensors for sensing said signal;

a measured data storage;

said measured data storage storing the measured data and their associate addresses and containing a null address storage at which the measured data associated with a starting point and an end point of each individual closed signal pattern are stored;

an analog-to-digital converter which is connected on its input side to the measuring unit and on its output side to the measured data storage;

means for determining a slope of each one of the individual closed signal patterns at a preselectable reference point and for transmitting the measured datum and address of the preselected reference point to the measured data storage;

a data and address bus operatively interconnecting the means for determining the preselected reference point and the measured data storage;

first sampling means for sampling a first sample of measured data and their associated addresses which precede the reference point in each one of the individual closed signal patterns;

second sampling means for sampling a second sample of measured data and their associated addresses which follow the reference point in each one of the individual closed signal patterns;

the first sampling means and the second sampling means being operatively connected to the measured data storage by means of the data and address bus;

means for sequentially determining the spatial distances between the measured data of the first sample and the measured data of the second sample;

comparing means operatively connected to the means for sequentially determining the spatial distances and comparing the determined spatial distances in order to determine a minimum spatial distance;

the comparing means being operatively connected to the measured data storage and transferring the measured datum of the first sample which is associated with the minimum spatial distance to the null address of the measured data storage; and a program sequencer operatively connecting the measured data storage, the slope determining means, the first sampling means, the second sampling means, and the comparing means and controlling the slope determination and the sampling and comparing operations.

The advantages achieved by the invention are essentially that the magnitude of the measured signal excursions can be exactly determined after the moments of time associated with the starting point and the end point have become known and therefrom also the signal magnitudes at these points have become known. The signal magnitude at the starting point and at the end point yields a reference magnitude. Also, different signals within a signal pattern can be precisely delimited from each other.

In a vector cardiogram the cardiac action of a person or patient investigated is observed by means of the temporal variations of the electromagnetic field which is generated by the heart and which can be represented by a vector. By means of the vector cardiogram attempts are made to follow the direction and magnitude of the vector. For this purpose the vector or rather its projection on a number of planes is considered. In practice this results in a number of temporally interrelated signal patterns. A reliable diagnosis and interpretation of the individual signals can be obtained only when the starting point and the end point of each individual signal of the different signal patterns are known. For the diagnosis there are also important, in addition to the magnitude and direction of the vector, the point of onset of the QRS-, P- and of the T-loop or wave, the starting moment of time and the length of the intervals therebetween.

By virtue of the inventive method and apparatus the aforementioned data can be determined. With increasing heart beat the results which are obtained using the hitherto known methods become more and more unreliable. The reliability of the inventive method, however, is preserved also in these cases of increased heart beat.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE PREFERRED EMBODIMENTS

Describing now the drawings, it is to be understood that only enough of the inventive method and apparatus have been illustrated as needed for those skilled in the art to readily understand the underlying principles and concepts of the present development, while simplifying the showing of the drawings. Turning attention now specifically to FIG. 1, there has been shown as an example of a physiological measuring signal a section of a vector cardiogram curve 1. Therein electrode potential values which are picked up from an investigated person or patient by means of electrodes, are plotted on a time axis 2. Since the inventive method will be explained with reference to the example of a vector which represents the heart action of a living being and which continuously changes its magnitude and direction as a function of time, the potential values illustrated in FIG. 1 can be considered as the magnitude of the vector projected into a predetermined plane.

Such a vector or the potential values associated with its tip or end point describes a time sequence of signal or electrode potential patterns each of which is described by the cardiologist as comprising a QRS-loop or wave, a T-loop or wave and a P-loop or wave. Sections 4 are interposed intermediate these loops or waves in curve 1 and these sections 4 are rather short and more or less indicate constant potential values.

Figure 2:
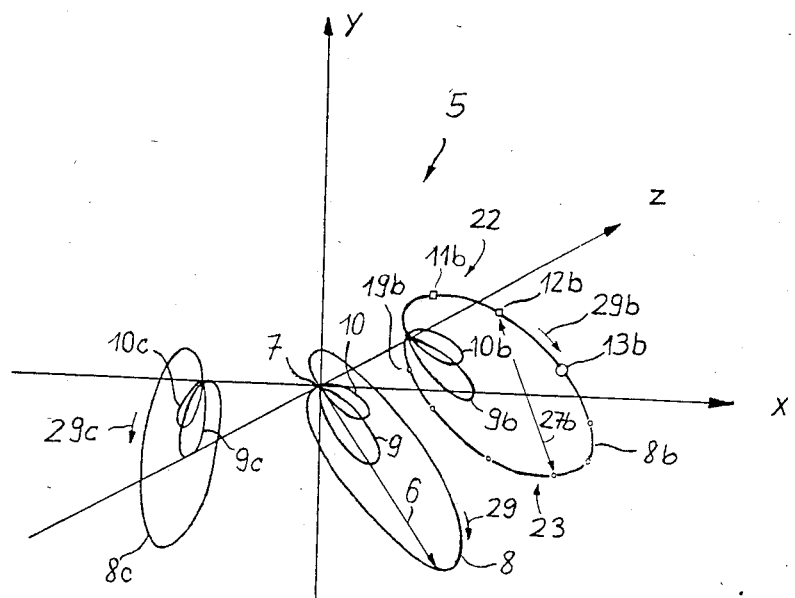
FIG. 2 is an illustration of the measured signal as shown in FIG. 1 in space as well as in projection on three different planes.
Figure 2:
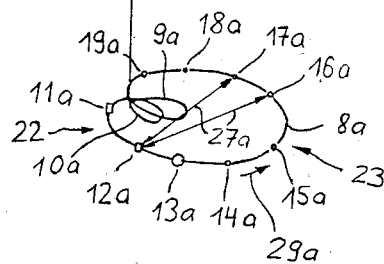

FIG. 2 shows the vector in a triaxial coordinate system 5 defining an orthogonal or rectangular coordinate system and illustrates the vector at a specific moment of time by means of the arrow 6. This vector 6 starts from a null or zero point 7 and ends at points in space which together form the loops or waves 8, 9 and 10. The loop 8 of such vectorial illustration is also designated as QRS-loop, the loop 9 as T-loop and the loop 10 as P-loop. By means of the X, Y and Z axes of the coordinate system 5 an XZ plane, an XY plane and a ZY plane are defined. The loops 8, 9 and 10 can be projected onto these three planes such that further loops 8a, 8b, 8c; 9a, 9b, 9c; and 10a, 10b, 10c can be recognized. In order to facilitate the following explanations there are also entered individual points 11a to 19a and 11b to 19b, along the loops 8a and 8b, respectively.

In the following there are generally described the individual steps of the inventive method which permits the determination of the starting point and of the end point of recurring individual spatial closed signal or electrode potential patterns, specifically of, for example, a QRS-loop in a vector cardiogram. Since the vector in each such vector cardiogram successively describes a QRS-loop, a T-loop and a P-loop, it is important to know, for example, at which point and at which time the QRS-loop starts and ends because the QRS-loop gives the physician an indication with respect to certain aspects of the cardiac action while the T-loop or the P-loop give indications with respect to other aspects of the cardiac action. The inventive method can be analogously employed for determining the starting point and the end point of the P-loop or wave and of the T-loop or wave in a vector cardiogram or the starting point and the end point of any other recurring individual closed signal or electrode potential pattern.

Figure 1:
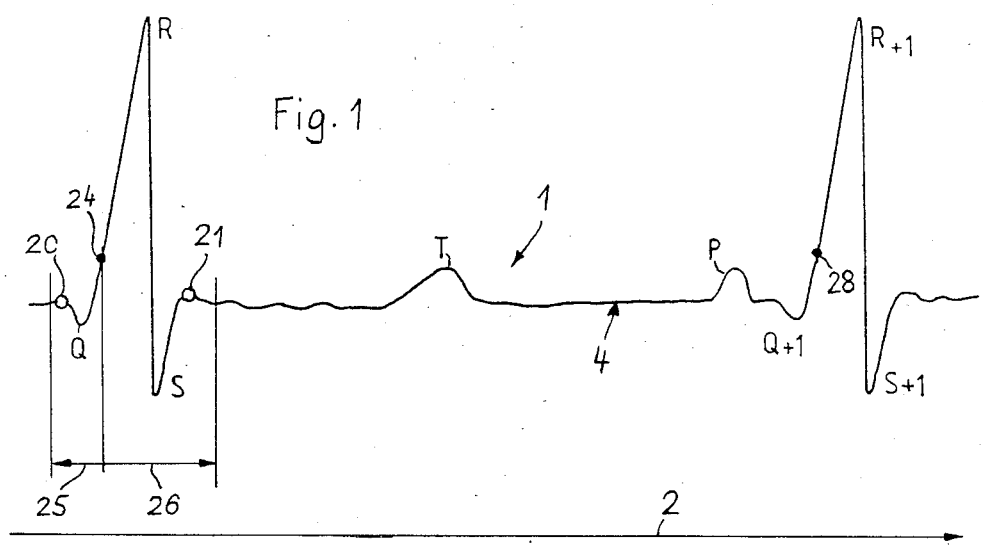
FIG. 1 is an illustration in a predetermined plane and along a time axis of a physiological measured signal which is picked up from a person or patient under investigation by means of electrodes.

In order to obtain reliable data about the position of the starting point 20 and the end point 21 of the QRS-wave or loop, see FIG. 1, it is essential to detect the movements of the vector and thus the QRS-loop 8, 8a, 8b, 8c in different planes. Therefore, during the preparation of a vector cardiogram, there are periodically or continuously detected in a manner which is known as such the values of the potential which is represented by the vector. The graphic illustration of such potential values, when plotted along the time axis 2, results in the curve 1 shown in FIG. 1. The graphic illustration of such potential values, when plotted in the XZ plane, in the XY plane, and in the ZY plane, results in the QRS-loops 8a, 8b, and 8c, respectively.

When the values of the potential are discontinuously or digitally detected by scanning or sampling the electrodes 60, the X-values, Y-values and Z-values of the electrode potential are detected and stored at predetermined scanning or sampling moments which represent the addresses of the related electrode potentials. A suitable combination of such potential values in two different axes, conjointly with the different scanning or sampling moments at which these values have been detected, results in the points 11a to 19a of the QRS-loop 8a, or, for example, of the points 11b to 19b of the QRS-loop 8b.

Slope values of the vector or of the preselected QRS-loop in a vector cardiogram are obtained from the differences of the potential values at two successive scanning or sampling moments. This operation can be separately performed for each one of the three planes of the coordinate system 5. Thus, for example, a slope value is determined for the region between the points 12a and 13a in the XZ-projection, for the points 12b and 13b in the XY-projection and so forth. This operation is performed using all scanned or sampled values of the QRS-loops 8a, 8b, and 8c. There are thus obtained three slope values, each associated with two successive points in one of the aforementioned regions. From the slope values thus obtained the slope in space or spatial slope is computed and an average value of the spatial slope is computed from all determined spatial slope values.

A comparison of the individual slope values with the average slope value permits, for example, to exclude slope values which exceed the average slope value by a predetermined extent and thus need not be further considered. A new average slope value is formed from the remaining slope values.

A spread or band width is defined for the new average slope value and the slope values of the vector should be reasonably expected to lie within this spread or band width. This spread is defined in order to exclude from consideration, for example, extrasystoles which occur in the heart and which have high slope values.

Subsequently, there is selected from successive slope values which have the same direction and which lie within the aforementioned spread or band width, the first slope value within the aforementioned spread or band width. The moment of time is determined which is associated with this slope value and at which the first one of the two potential values has been detected which were required for the computation of the slope. This moment of time also may be designated as or represents a reference point 24 and serves the purpose of subdividing the QRS-loop or the projections 8a, 8b, 8c thereof into a first section 22 and a second section 23. In the illustration according to FIG. 2 the points designated by 13a and 13b correspond to this moment of time or reference point 24. This reference point 24 serves as the reference for further considerations or measurements at the QRS-loop or wave or at the entire heart beat period.

A predetermined first time interval 25 and a predetermined second time interval 26 are defined and extend from the moment of time or reference point 24 or the corresponding points 13a, 13b. The first time interval 25 precedes the moment of time or reference point 24 and the second time interval 26 follows the moment of time or reference point 24 or the corresponding points 13a, 13b and so forth. For investigating the human heart the first time interval 25 preferably encompasses 60 milliseconds and the second time interval 26 a maximum of about 200 milliseconds. The first time interval 25 may be in the range of 60 to 140 milliseconds and the second time interval 26 may be in the range of 160 to 200 milliseconds. The sections 22 and 23 which respectively precede or follow the points 13a, 13b and so forth in the illustration according to FIG. 2 correspond to the time intervals 25 and 26 according to FIG. 1. The arrows 29, 29a, 29b, 29c indicate the time sequence or course of the loops or signal patterns 8, 8a, 8b, and 8c.

In a further step of the inventive method there are now determined the distances 27a, 27b and so forth between the points 11a, 12a, 11b, 12b and so forth of the first section 22 and the points 14a to 19a, 14b to 19b and so forth of the second section 23 of the QRS-loop or wave 8a, 8b, and so forth. The distances 27a, 27b and so forth which are determined between the tips or end points of the vector in the first and second sections 22 and 23 can be calculated, for example, in a triaxial coordinate system in accordance with the known formula:

$$a = \sqrt{(X_1 - X_2)^2 + (Y_1 - Y_2)^2 + (Z_1 - Z_2)^2}$$

for two points which are designated by the indices 1 and 2.

The values which are thus obtained for the spatial distances between all possible combinations of two points in the first and second sections 22 and 23 are now investigated for the minimum spatial distance. Each one of the two points between which the minimum distance exists and which may be assumed, for example, to be the points 11 and 19, 11a and 19a, 11b and 19b and so forth, is associated with a related scanning or sampling moment of time. These scanning or sampling moments of time of the two points which have the minimum distance therebetween are now respectively defined as the starting point 20 and as the end point 21 of the QRS-loop or wave or as zero points 7 of the QRS-loop.

The method described hereinbefore is particularly well suited in instances in which all data are first detected and evaluated subsequently. However, the method can also be adapted to an immediate continuous or on-line data evaluation which is performed already during the data detection and storage.

For this purpose, for example, a fixed slope value can be predetermined for the first detected heart beat. The first detected slope value which equals this predetermined slope value yields a scanning or sampling moment of time which is set as the moment of time or as a first reference point. Starting from this thus determined reference point, the starting point and the end point of the QRS-wave are determined in the already known manner.

For the second heart beat of the series of measurements an improved assumption can be made for the reference point by determining, after the reference point of the first heart beat, the maximum slope occurring in the same direction and considering the associated scanning or sampling moment of time as the new reference point for the second heart beat.

Furthermore, the time duration between the now known first and new reference points of the first heart beat and of the second heart beat, respectively, can be measured and plotted while starting from the starting point and the end point of the first heart beat. As a matter of simplification in the illustration of the drawings such first and new reference points have been designated in FIG. 1 by reference characters 24 and 28, respectively. In this manner the starting point and the end point of the second heart beat are obtained.

In this manner, the determination of the moment of time or reference point and, on the basis thereof, the determination of the starting point and of the end point of the QRS-loop or wave can be continuously improved. As a result of this procedure there are unobjectionably established for each heart beat or, generally, for each period of the physiological signal under consideration, the starting point and the end point of the signal or of different signal portions with respect to their occurrence in time as well as with respect to their electric potential which is derived therefrom. It will be recognized that this method is particularly suited for evaluating the detected data by means of a data processing system or by means of a computer.

Figure 3:
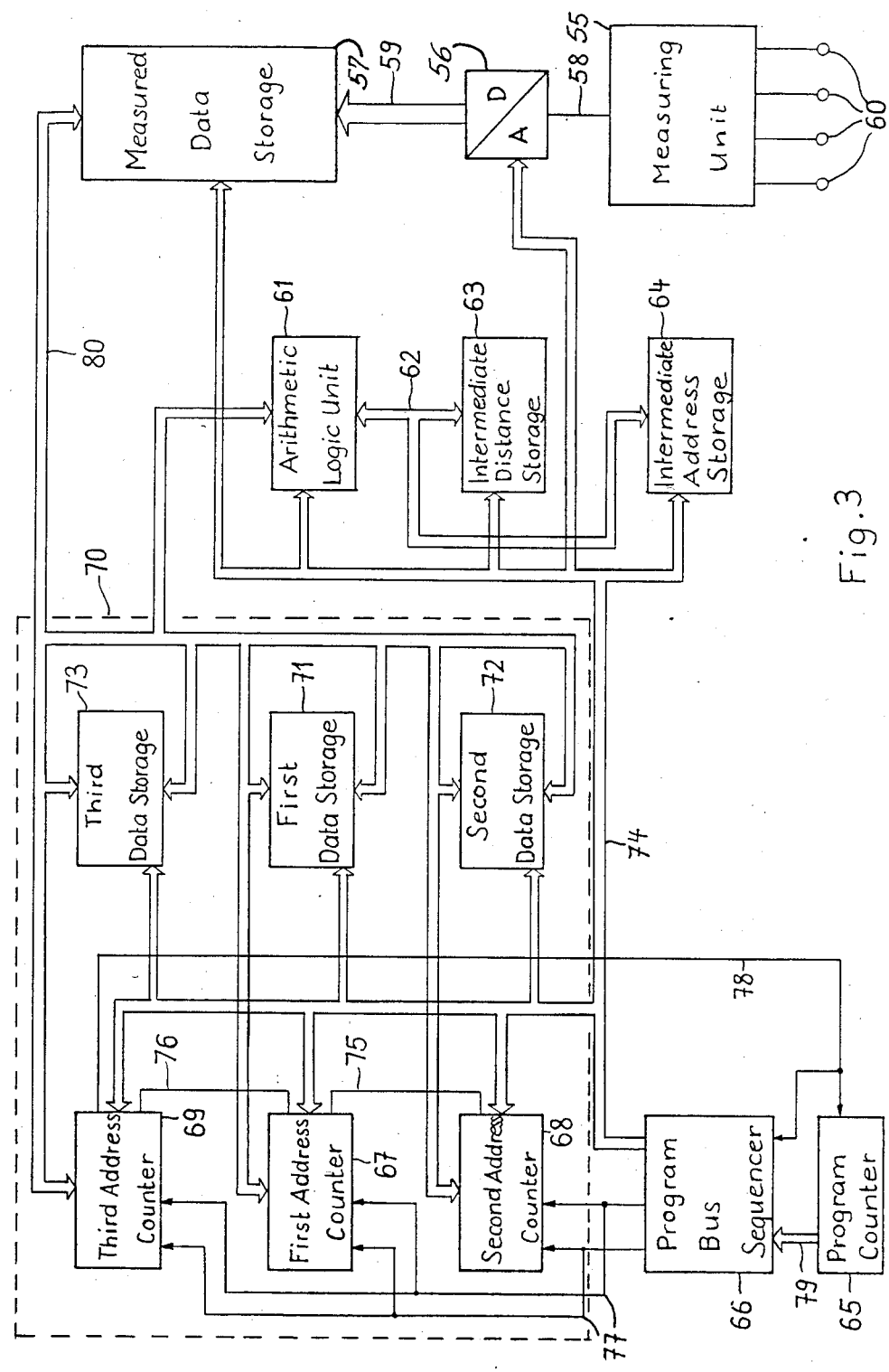
FIG. 3 is a block diagram of an apparatus according to the invention for carrying out the method illustrated in FIGS. 4a, 4b, and 4c.

FIG. 3 of the drawings shows a block circuit diagram of an exemplary embodiment of the inventive apparatus for recording and processing a measured signal constituted by measured data which vary in time and space and define a time sequence of recurring individual closed signal patterns. Such apparatus is suited to perform the steps of the method which has been generally described hereinbefore, specifically with regard to physiological measured signals like, for example, the recurring individual spatial closed electrode potential patterns of a vector cardiogram of the exemplary embodiment.

The main elements of the inventive apparatus illustrated in FIG. 3 constitute a measuring unit 55, an analog-to-digital converter 56 and a measured data storage 57. Electrodes 60 are arranged in the predetermined configuration required to pick up the variation of a potential in space and time as is known, for example, for picking up the potential variations associated with cardiac action. The electrodes 60 are connected in known manner to the input side of the measuring unit 55. The analog-to-digital converter 56 of conventional construction is connected on its input side to the measuring unit 55 by means of a conductor 58 and is further connected on its output side to the measured data storage 57 by means of a bus 59. The measuring unit 55 comprises a conventional circuit for detecting and, if necessary, filtering the individual measured data or electrode potentials received from the electrodes 60 and, therefore, is not illustrated in any particular detail. From the potential differences measured at the individual electrodes 60, the measured values or electrode potentials with respect to the X, Y and Z axes of the triaxial coordinate system 5, see FIG. 2, are determined according to a procedure as known, for example, from the aforementioned European Patent Publication No. 0,086,429 and the corresponding commonly assigned and copending, initially cross-referenced U.S. Application Ser. No. 06/464,765. The values of the potential as determined in the individual coordinates X, Y, Z of the triaxial coordinate system 5 are designated as the measured values or data. The measured data storage 57 comprises a random-access-memory of sufficient capacity to store a number of measured data as well as a number of results computed therefrom.

In a specifically preferred design of the illustrated exemplary embodiment a suitable arithmetic logic unit ALU designated by the reference numeral 61 performs all the computations needed in carrying out the method as described hereinbefore. Such arithmetic logic units are known as such and commercially available. Two intermediate storages, namely an intermediate distance storage 63 and an intermediate address storage 64, are connected to the arithmetic logic unit 61 by means of a bus 62. The intermediate storages 63 and 64 serve to temporarily store individual intermediate values which are needed for the evaluation, particularly for the determination of the starting point and of the end point of the recurring individual spatial signal or electrode potential patterns.

As further main elements there are considered a program counter 65 and a program bus sequencer 66 which is designed as a read-only-memory. The program counter 65 is activated by means of a clock signal and, by counting, causes a program instruction to be read-out from the program sequencer 66 at each state of the program counter 65, which is connected to the program sequencer 66 by means of a bus 79. The program sequencer 66 comprises a storage which stores all the program steps which are continuously addressed by the program counter 65. The program sequencer 66 thus is enabled to give the other elements of the apparatus the appropriate instructions for carrying-out the steps of the inventive method. The program sequencer 66 is of conventional structure and, therefore, not described in any particular detail.

A program bus 74 connects the program sequencer 66 to the measured data storage 57, the arithmetic logic unit 61, to the analog-to-digital converter 56 and to a sampling unit 70 comprising first, second and third data storages 70, 71, 72 and associated first, second and third address counters 67, 68, 69. A conductor 78 connects the program counter 65 to the program sequencer 66 and to the third address storage 69 and further conductors 77 connect the program sequencer 66 with the address counters 67, 68, and 69. A conductor 75 interconnects the first and second address counters 67 and 68 and a further conductor 76 interconnects the first and third address counters 67 and 69. A data and address bus 80 is provided for transferring measured data, computed results, intermediate values and addresses thereof and this data and address bus 80 connects the sampling unit 70 and its elements such as the storages 70, 71, 72 and counters 67, 68, 69 as well as the arithmetic logic unit 61 to the measured data storage 57.

It will be evident to a person skilled in the art that further connections are made between the different components of the inventive apparatus, for example, for transmitting clock signals because such apparatus as described herein is controlled by means of clocks, as is generally known. Such clocks define a very fine time slot pattern within which the individual instructions are given and individual operations are conducted.

An exemplary embodiment of the inventive method will now be explained with reference to the individual method steps which are explained in the flow chart shown in FIGS. 4a, 4b and 4c and during this description reference will also be made to the block circuit diagram of the inventive apparatus illustrated in FIG. 3.

The reception and recordal of electrode potentials and the transformation of the electrode potentials into the measured data stored in the measured data storage 57 is known, for example, from the aforementioned European Patent Publication No. 0,086,429 and the commonly assigned, copending initially cross-referenced U.S. patent application Ser. No. 06/464,765, and thus does not here require any detailed description. The measured data are digitized in an also known manner by means of the analog-to-digital converter 56 and are supplied and read into the measured data storage 57 by means of the bus 59. This operation corresponds to the method step 31 which is shown in FIG. 4a.

In order to determine the reference moment of time or reference point 24 of a preselected loop like the QRS-loop or wave in an individual spatial closed signal or electrode potential pattern like a vector cardiogram, slope values are determined between two successive measured data and their related scanning or sampling times. For this purpose first measured data related to the three axes X, Y, Z of the coordinate system 5 are read-out from the measured data storage 57 and are supplied to the arithmetic logic unit 61 by means of the data and address bus 80. Slope values between the two successive such measured data are computed in the arithmetic logic unit 61 for each one of the X, Y and Z axes in accordance with the formula:

$$f(x,y,z,t) = \sqrt{[x(t+T) - x(t)]^2 + [y(t+T) - y(t)]^2 + [z(t+T) - z(t)]^2}$$

Therein t designates the moment of time associated with the measured data with respect to the X, Y, and Z axis and T designates a scanning or sampling interval. In the specific embodiment relating to the QRS-loop or wave in a vector cardiogram the electrode potentials are measured during a predetermined time interval of, for example, one second duration. The time T between two successive measured electrode potentials corresponds to the reverse of the digitizing frequency which is determined by the A-D converter 56 as 750 Hz. From the thus obtained spatial slope values there is determined a maximum positive slope value and transferred to the measured data storage 57 via the data and address bus 80. These operations are controlled in a manner which is known as such by means of the program sequencer 66 and the program bus 74. This step of the inventive method is designated 32 in FIG. 4a.

Figure 4A:
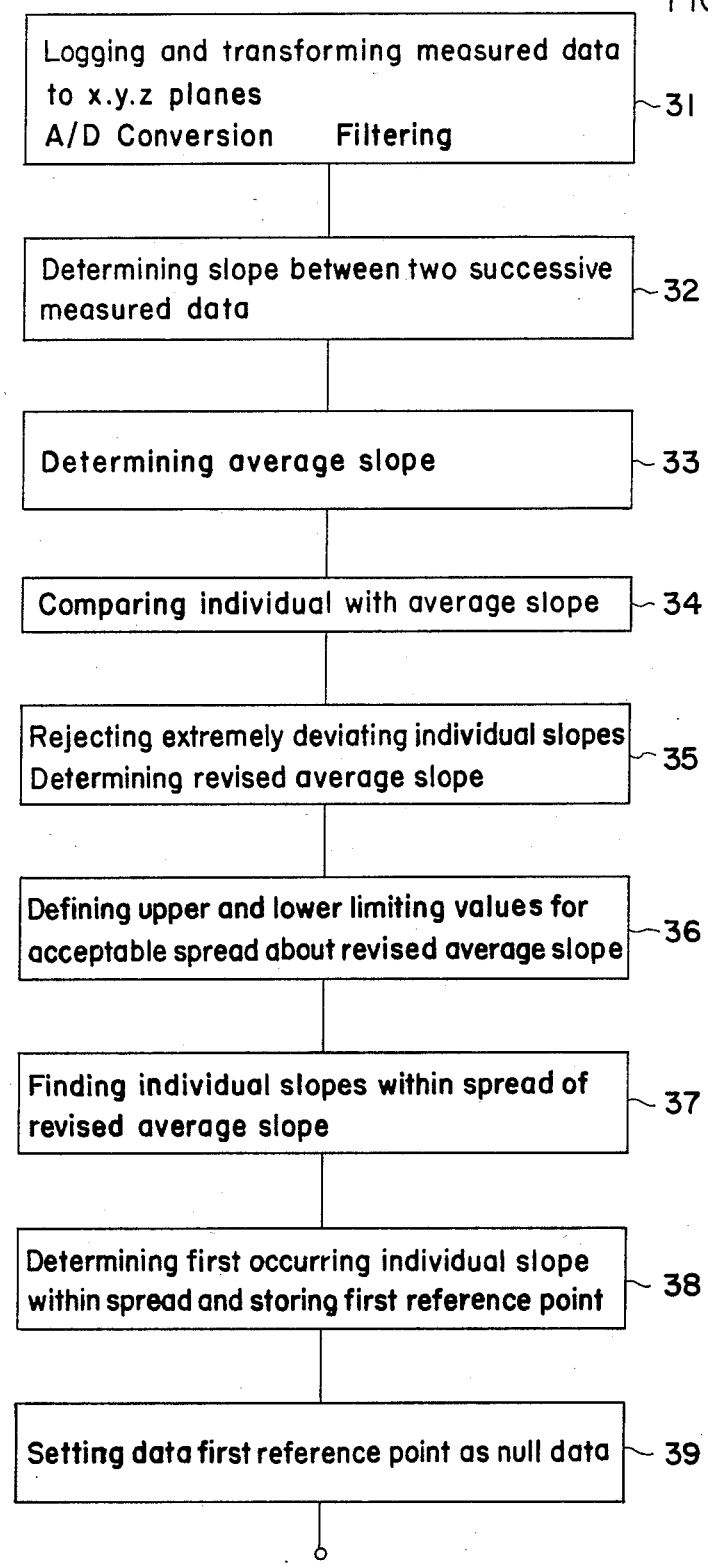
FIGS. 4a, 4b, and 4c collectively represent a flow diagram or chart illustrating the steps of the inventive method.

From the maximum positive slope values f determined for a number of QRS-loops of individual spatial closed signal or electrode potential patterns or vector cardiograms an average value M of the spatial slope is determined in an analogous manner in the arithmetic logic unit 61 and this method step is designated 33 in FIG. 4a. The determination is made according to the formula:

$$M = \frac{1}{N} \cdot \sum_{i=1}^{N} f(x,y,z,t)$$

wherein N is the number of determined maximum positive spatial slope values f.

In the further method steps which are designated 34 and 35 in FIG. 4a and which are are also performed by means of the arithmetic logic unit 61, the determined maximum positive spatial slope values f are compared with the average value M in a comparator which constitutes part of the arithmetic logic unit 61. Slope values f are thus detected and then eliminated which deviate extremely from the average value M. A revised average value M' for the spatial slope is thereby obtained and this revised average value M' is unaffected by extreme slope values which possibly are due to errors or accidents.

Subsequently and in accordance with method step 36 in FIG. 4a, a spread or band width about the revised average spatial slope value M' is determined and this spread or band width is limited by an upper limiting value UV and a lower limiting value LV. The limiting values UV and LV are read into the measured data storage 57.

By a comparison of the stored maximum positive spatial slope values f with the lower limiting value L.V and the upper limiting value UV in the comparator of the arithmetic logic unit 61 there are selected individual spatial closed signal or electrode potential patterns or vector cardiograms with QRS-loops or waves having maximum positive spatial slope values f which lie within the spread or band width. The first vector cardiogram occurring in time and having a QRS-loop with a maximum positive spatial slope within this band width is determined. The moment of time t or the address of the measured datum or electrode potential which is stored in the measured data storage 57 and which is associated with this first maximum positive spatial slope value f, is set as a trigger point or reference point 24 and read into the third address counter 69 via the data and address bus 80. The measured datum or electrode potential which is stored in the measured data storage 57 and associated with this address is read into the third data storage 73 via the data and address bus 80. Furthermore, the address or the moment of time associated with this measured datum or electrode potential is read into a null address in the measured data storage 57. These steps are numbered 37, 38 and 39 in FIG. 4a. The reference points are determined for all of the selected individual spatial closed signal or electrode potential patterns or vector cardiograms and are stored in the third data storage 73. The addresses or moments of time related to the different reference points are stored in the third address counter 69.

Figure 4B:
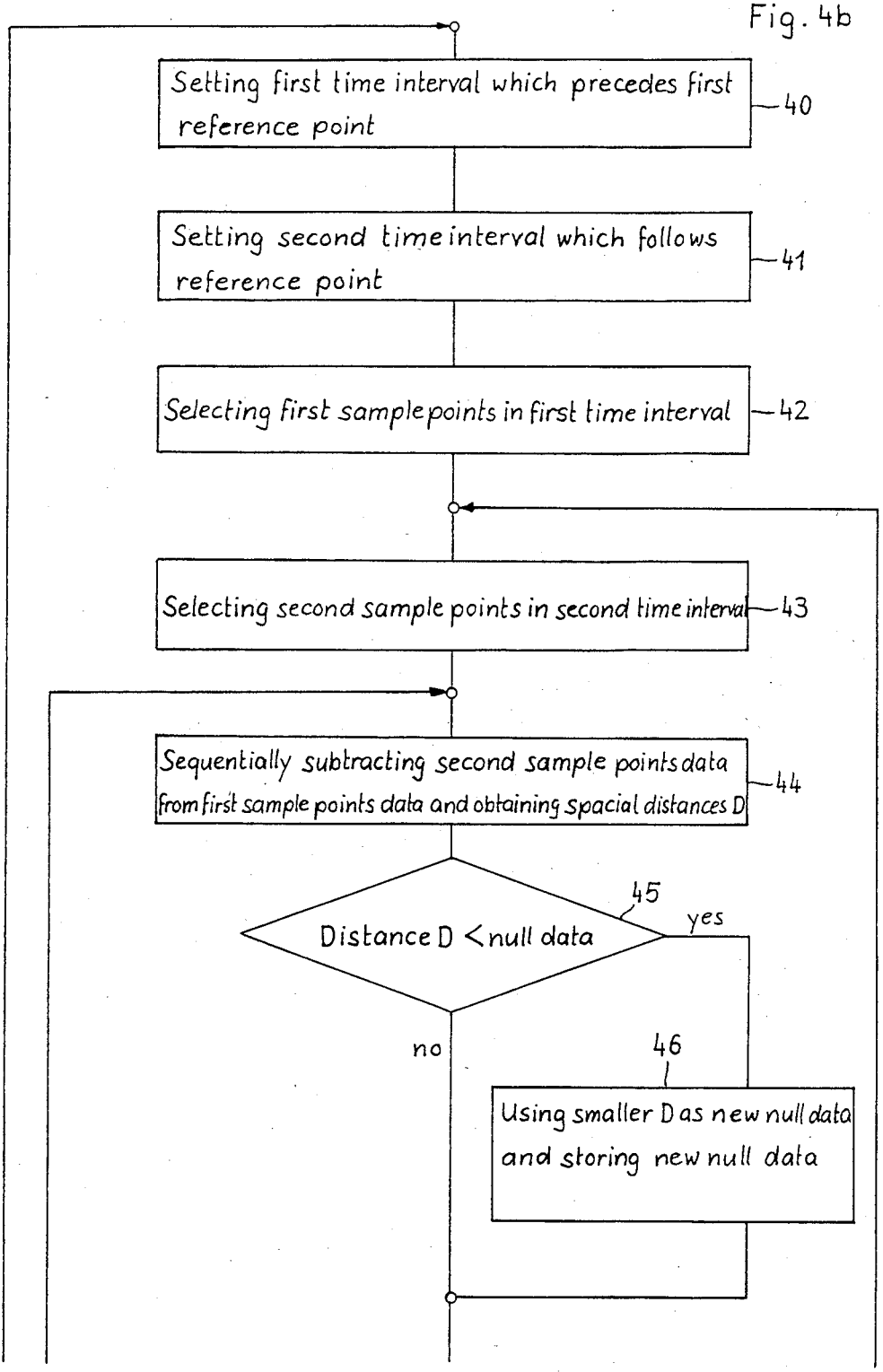
Figure 4C:
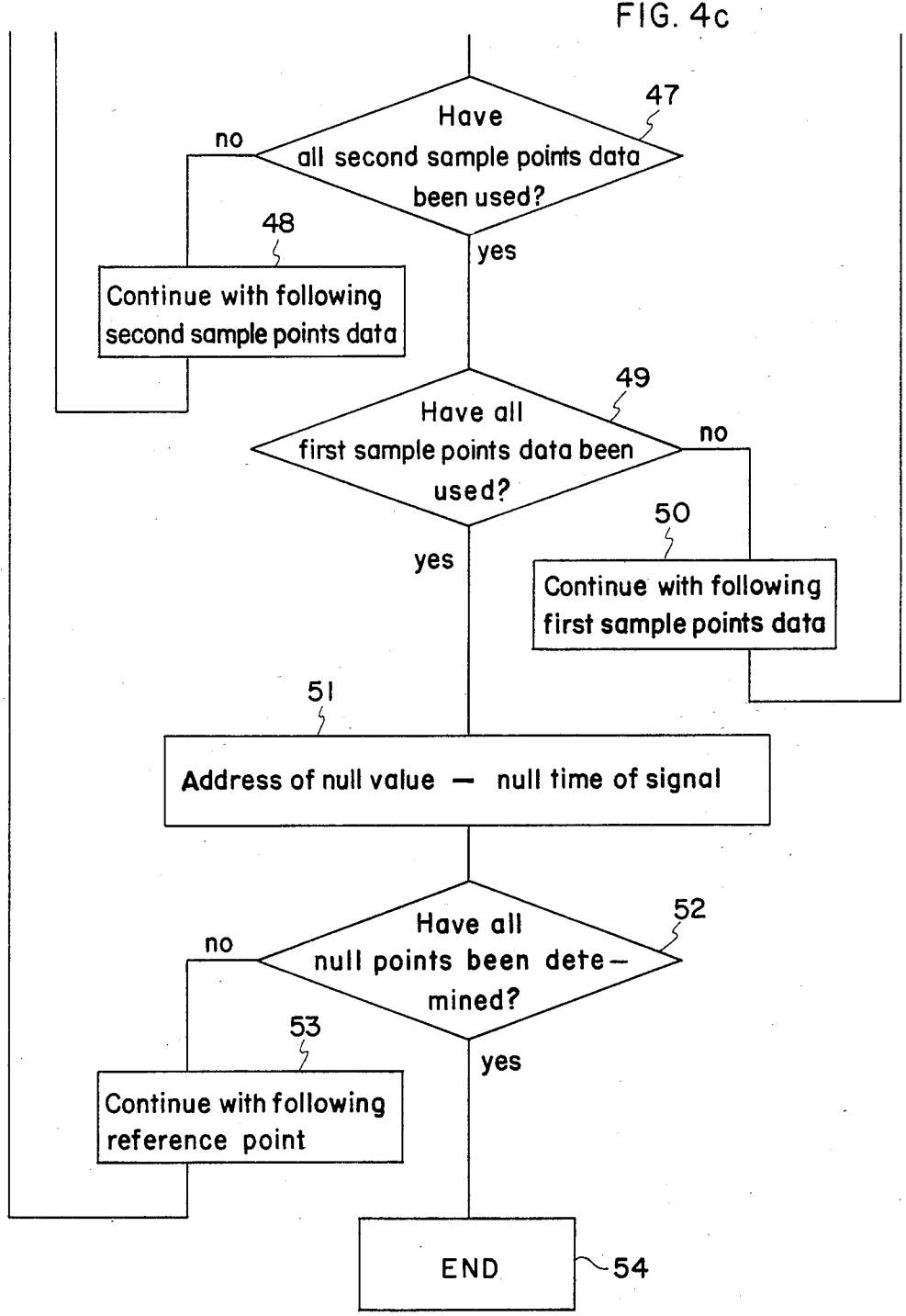

In accordance with the steps numbered 40 and 41 in FIG. 4b, a first sample of measured data is sampled by means of the sampling unit 70 which measured data or electrode potentials are associated with the first time interval 25 which precedes the trigger point or reference point 24, and a second sample of further measured data or electrode potentials is sampled which are associated with the second time interval 26 following the trigger point or reference point 24. In the specifically described embodiment relating to the QRS-loop or wave in a vector cardiogram the first time interval 25 extends from a preselected moment of time preceding the reference point 24 by about 20 milliseconds to a first moment of time preceding the reference point 24 by a time period of preferably 80 preselected moment of time following the reference point 24 by about 20 milliseconds to a second moment of time following the reference point 24 by a time period of preferably 200 milliseconds. The time periods 25 and 26 can be selected such that the entire useful range in which measured data are evaluated has a duration in the range of 60 to 140 and 160 to 200 milliseconds, respectively. The aforementioned measured data or electrode potentials are read into the first and second data storages 71 and 72, respectively, via the data and address bus 80. The data storage 71 thus contains the measured data or electrode potentials associated with the first time interval 25 while the second data storage 72 contains the measured data or electrode potentials associated with the second time interval 26. By dividing a related one of the time intervals 25, 26 by the total sampling interval or sampling time the number of measured data or electrode potentials is obtained which have to be subtracted or added to the measured datum associated with the trigger point or reference point 24. Like the spread or band width of the spatial slope values the sampling interval or time is entered into the measured data storage 57.

The addresses or moments of time associated with the measured data or electrode potentials of the respective time intervals 25, 26 are respectively read into the first and second address counters 67 and 68 in the same manner as described hereinbefore for the address of the trigger point or reference point 24 and the third address storage 69. Thus, the first address storage 67 contains the addresses or moments of time of the measured data or electrode potentials associated with the first time interval 25 and stored in the first data storage 71, while the second address counter 68 contains the addresses or moments of time of the measured data or electrode potentials associated with the second time interval 26 and stored in the second data storage 72. Each counter reading or state in the address counters 67, 68 and 69 is associated with an address or moment of time such that a related address or moment of time is read-out via the data and address bus 80 whenever this counter reading or state is reached during a counting procedure. By means of this address or moment of time the associated measured datum can be read-out from one of the data storages 71, 72 and 73. Thus, the counter reading or state of the address counters 67, 68 and 69 represents an address for a further address.

The first measured datum or electrode potential or the X, Y and Z coordinates thereof which are associated with the first time interval 25 is read-out from the first data storage 71 and read into the arithmetic logic unit 61 via the data and address bus 80. The same is done for the first measured or electrode datum potential associated with the second time interval 26 and stored in the second data storage 72. In this manner the method steps 42 and 43 in FIG. 4b are performed.

In the arithmetic logic unit 61 the spatial distance D between the aforementioned first measured data or electrode potentials is computed in accordance with the formula:

$$D = \sqrt{(x_{11} - x_{12})^2 + (y_{11} - y_{12})^2 + (z_{11} - z_{12})^2}$$

This is the method step 44 in FIG. 4b and, during this step, the determined spatial distance D is read into the intermediate distance storage 63. In addition, a related address associated with the thus determined distance D is read into the intermediate address storage 64 via the bus 62.

In a first variant of the exemplary embodiment of the inventive method the spatial distances D determined in the manner as described hereinbefore are compared with each other by means of the comparator of the arithmetic logic unit 61 in order to determine the minimum spatial distance. The addresses associated with the measured electrode potential of the first sample and the measured electrode potential of the second sample, which are associated with the minimum spatial distance, are respectively defined as the starting point 20 and the end point 21 of the QRS-loop or wave of the investigated vector cardiogram. These addresses are stored in the measured data storage 57 under the null address thereof. The starting point 20 also defines the starting point of the entire vector cardiogram cycle.

A second variant of the exemplary embodiment of the inventive method will be described hereinafter and this second variant has the advantage of an improved consideration of noise in the determination of the starting point and of the end point of, for example, the QRS-loop or wave in a vector cardiogram. According to this method the greatest measured electrode potential of the QRS-loop or wave under investigation is stored under the null address in the measured data storage 57. The comparator in the arithmetic logic unit 61 performs a comparison between the just determined spatial distance D and the null or zero value which is stored at the null address in the measured data storage 57 and which is supplied therefrom by means of the data and address bus 80. In the first run this spatial distance D certainly will be smaller than the null or zero value stored at the null address in the measured data storage 57 and, therefore, the just determined spatial distance D replaces the null or zero value and is stored under the null address in the measured data storage 57. The addresses of the two measured data or electrode potentials from which the spatial distance D has been determined, are designated as the null addresses or moments of time and are also stored in the measured data storage 57. Accordingly, steps 45 and 46 of the inventive method shown in FIG. 4b have been performed.

The same steps and comparisons are performed using the remaining first measured data or electrode potentials in the first data storage 71 and the associated addresses or moments of time stored in the first address counter 67.

According to the method step 47 there will be examined during this process whether the first address counter 67 has arrived at the counter reading or state zero. A related counting value is allocated to each one of the address counters 67, 68 and 69 of the sampling unit 70 via the program sequencer 66 and the conductor 77 and each one of the aforementioned counters counts backwards from this allocated counting value to zero. The counter reading or state corresponds to the number of measured data or electrode potentials which have been stored in the data storages 71, 72 and 73 of the sampling unit 70. When the first address counter 67 has arrived at the counter reading or state zero, this first address counter 67 is reset to start counting again from the original counter reading or state and thereby the reading or state of the next-following or second address counter 68 is decreased by one unit via the conductor 75. The same applies to the first and third address counters 68 and 69 which are connected by the conductor 76.

When not all measured data or electrode potentials associated with the second time interval 26 have been used up and when thus the second address counter 68 has not arrived at the reading or value zero, the operation starts again with the method step 44 and a further measured datum or electrode potential associated with the second time interval 26 is selected for determining spatial distances D using the measured data or electrode potentials associated with the first time interval 25.

When all the measured data or electrode potentials associated with the second time interval 26 have been used up, the method step 49 is performed and during this method step there is examined whether all measured data or electrode potentials associated with the first time interval 25 have been used up. When this is not the case, the method steps 43 to 50 are repeated until the second address counter 68 has arrived at a null or zero reading. When this is the case, the method step 51 is initiated and this step includes reading out the null or zero data from the measured data storage 57 which are stored therein at this time and which represent the electrode potentials and their related addresses which are associated with the minimum spatial distance D. The electrode potentials are read into the first and second data storages 71 and 72 which now also store the measured data or electrode potentials associated with the minimum spatial distance D and thus the measured data or electrode potentials at the starting point and at the end point. The related addresses are stored at the null address in the measured data storage 57 and respectively represent the starting point and the end point of the QRS-loop or wave of the first one of the selected individual spatial closed signal or electrode potential pattern or vector cardiogram which is associated with the first occurring trigger point or reference point 24 at which the spatial slope value lies within the predetermined spread or band width of spatial slope values.

In order to determine the zero positions or the starting and end points of the QRS-loops of further spatial closed signal or electrode potential patterns or vector cardiograms, the method is restarted with the steps 53 and 40 with regard to a further vector cardiogram with a QRS-loop or wave having a maximum spatial slope within the predetermined spread or band width. When the third address counter 69 also has arrived at the reading null or zero, the test according to method step 52 is affirmed and the procedure is concluded. The zero positions of all selected individual spatial closed signal or electrode potential patterns are now available in a storage, namely the measured data storage 57, and can be used for further processing the measured data or electrode potentials received by the electrodes 60.

While there are shown and described present preferred embodiments of the invention, it is to be distinctly understood that the invention is not limited thereto, but may be otherwise variously embodied and practiced within the scope of the following claims. Accordingly,

What we claim is:

1. A method of determining the starting point and the end point of a spatial closed signal pattern in a time sequence of individual ones of such spatial closed signal patterns, each of which is constituted by a series of measured signals, said method comprising the steps of:
   arrangiang a predetermined number of electrodes in a predetermined configuration at a living being to be investigated and receiving said time sequence of spatial closed signal patterns by means of said electrodes;
   subdividing a predetermined period of time which is associated with a selected one of said individual spatial closed signal patterns, into a first time interval and a second time interval;
   sampling said selected individual spatial closed signal pattern and determining, at each one of a predetermined number of sampling moments associated with said first time period, the distance between a predetermined number of sampling points associated with said predetermined number of sampling moments in said first time interval, on the one hand, and a predetermined number of sampling points associated with a predetermined number of sampling moments in said second time interval, on the other hand;
   ascertaining the minimum value of said distances determined between said predetermined sampling points associated with said first time interval and said predetermined sampling points associated with said second time interval; and
   defining a selected sampling point associated with said first time interval and a selected sampling point associated with said second time interval, between which said minimum distance exists, as said starting point and as said end point, respectively, of said selected individual spatial closed siqnal pattern.

2. The method as defined in claim 1, further including the step of:
   selecting a reference point by means of which said first time interval and said second time interval are separated from each other.

3. The method as defined in claim 1, wherein:
   the step of subdividing said predetermined period of time which is associated with said selected individual spatial closed signal pattern into said first time interval and said second time interval, entails the step of fixing said first time interval and said second time interval by means of a common moment of time at which a spatial slope of said selected individual spatial closed signal pattern has a predetermined value.

4. The method as defined in claim 3, further including the step of:
   presetting a predetermined spatial slope value for said spatial slope of said selected individual spatial closed signal pattern at said common moment of time;
   determining said common moment of time which fixes said first time interval and said second time interval, in a first approximation, by the moment of time at which the spatial slope of a first one of said time sequence of individual spatial closed signal patterns has a spatial slope value essentially equal to said preset predetermined spatial slope value;

determining individual spatial slope values of further individual spatial closed signal patterns following said first individual spatial closed signal pattern in said time sequence; and determining an average spatial slope value from said individual spatial slope values determined for said further individual spatial closed signal patterns and using such average value for presetting said predetermined spatial slope value for each one of said individual spatial closed signal patterns at said common moment of time.

5. The method as defined in claim 1, further including the steps of:

projecting each one of said individual spatial closed signal patterns into an orthogonal coordinate system; and determining spatial distances in said orthogonal coordinate system into which each said individual spatial closed signal pattern has been projected.

6. A method of recording a measured signal constituted by measured data which vary in time and space and form a time sequence of recurring individual spatial closed signal patterns, said method comprising the steps of:

receiving and recording as a function of time the measured data which constitute said measuring signal;

selecting a reference point for each one of said recurring individual spatial closed signal patterns;

determining, on the basis of said selected reference point, for each one of said recurring individual spatial closed signal patterns, a first time interval and a second time interval located at opposite sides of said reference point;

sampling a preselectable number of first measured data and related first moments of time which are associated with said first time interval and sampling a preselectable number of second measured data and related second moments of time which are associated with said second time interval;

determining the spatial distance between the measured data associated with said sampled first measured data and the measured data associated with said sampled second measured data; and determining a pair of sampled first and second measured data with which a minimum value of said spatial distance is associated and thereby ascertaining a starting point and an end point for each one of said recurring individual spatial closed signal patterns.

7. The method as defined in claim 6, further including the steps of:

placing a predetermined number of sensors in a predetermined spatial configuration at an object to be investigated; and the step of receiving and recording said measured data as a function of time entailing the step of receiving and recording the variation in time and space of a predetermined characteristic of said object by means of receiving and storing measured data which are measured by said sensors and which vary in time and space in correspondence with said predetermined characteristic of said object to be investigated.

8. The method as defined in claim 7, wherein:

said step of selecting said reference point includes the step of selecting, in a selected one of said recurring individual spatial closed signal patterns, a point at which said selected individual spatial closed signal pattern has a predetermined spatial slope.

9. The method as defined in claim 8, wherein:

said step of selecting said reference point includes the step of selecting as said reference point a point at which said selected individual closed signal pattern has a maximum spatial slope.

10. The method as defined in claim 9, wherein:

said step of selecting said point at which said selected individual spatial closed signal pattern has a maximum spatial slope, includes the step of selecting a predetermined time interval substantially encompassing said selected individual spatial closed signal pattern and subdividing said time interval into a sequence of successive sections, determining the spatial slope in each one of said successive sections and selecting the section having a maximum spatial slope; and defining the first occurring moment of time associated with said section having the maximum slope as said point constituting said reference point.

11. The method as defined in claim 10, further including the steps of:

repeating the determination of the maximum spatial slope of said individual spatial closed signal pattern for different ones of said sequence of said individual spatial closed signal patterns; and determining an average value of the maximum spatial slope of the individual spatial closed signal patterns from the maximum spatial slopes determined for said different individual spatial closed signal patterns and for the selected individual spatial closed signal patterns.

12. The method as defined in claim 11, further including the step of:

defining a predetermined upper value and a predetermined lower value of said maximum spatial slope and thus a predetermined spread of acceptable values for said maximum spatial slope of said individual spatial closed signal patterns at said reference point.

13. The method as defined in claim 7, wherein:

said step of determining said first time interval includes the step of selecting as said first time interval a time interval which extends from the moment of time associated with said reference point to a preceding moment of time in the region of the starting point of said selected individual spatial closed signal pattern; and said step of determining said second time interval including the step of selecting as said second time interval a time interval extending from said moment of time associated with said reference point to a following moment of time in the region of the end point of said selected individual spatial closed signal pattern.

14. The method as defined in claim 7, wherein:

said step of placing a predetermined number of sensors in a predetermined spatial configuration at an object to be investigated includes the step of placing a predetermined number of electrodes in said predetermined spatial configuration at the body of a living being; and the step of receiving and recording said measured data including the step of measuring and recording the variation in time and space of an electric potential which occurs in said living being, in the form of a vector diagram constituted by a time sequence of recurring individual spatial closed electrode potential patterns which are constituted by a predetermined number of loops and which are received and recorded in a rectangular coordinate system defined by said predetermined spatial configuration of said predetermined number of electrodes.

15. The method as defined in claim 14, further including the steps of:

scanning said predetermined number of electrodes at a predetermined scanning frequency; and feeding said measured electrode potentials measured at related scanning moments of time via an analog-to-digital converter to a measured data storage and storing therein said measured individual spatial closed electrode potential patterns in digital form at associated addresses which correspond to the related scanning moments of time.

16. The method as defined in claim 15, further including the steps of:

operatively connecting said measured data storage to an arithemetic logic unit;

transmitting successively measured electrode potentials mesured at related scanning moments of time within a predetermined time interval substantially including a preselected loop of a selected individual spatial closed electrode potential pattern from said measured data storage to said arithemetic logic unit and determined by means of two of said successively measured electrode potentials and two of said related scanning moments of time a predetermined slope of said preselected loop in said rectangular coordinate system;

determining a predetermined spatial slope of said preselected loop of said selected individual spatial closed electrode potential pattern from the predetermined slopes in said rectangular coordinate system;

defining as said reference point the first occurring scanning moment of time associated with said predetermined spatial slope; and transmitting said predetermined spatial slope of said preselected loop of said selected individual spatial closed electrode potential pattern to said measured data storage.

17. The method as defined in claim 16, wherein:

said step of determining said predetermined slope of said preselected loop in said rectangular coordinate system entails the step of determining by means of two successively measured electrode potentials and two of said related scanning moments of time a maximum variation in the electrode potential with time and thus a maximum slope;

said step of determining the predetermined spatial slope of said preselected loop entails the step of determining the maximum spatial slope; and said step of transmitting said predetermined spatial slope entails the step of transmitting said maximum spatial slope of said preselected loop to said measured data storage.

18. The method as defined in claim 17, wherein:

said steps of determining and transmitting said maximum spatial slope of said preselected loop of said selected individual spatial closed electrode potential pattern includes the step of determining and transmitting the maximum positive spatial slope.

19. The method as defined in claim 18, wherein:

said step of placing a predetermined number of electrodes and measuring and recording the variation in time and space of the electrode potential includes the step of picking up a time sequence of recurring vector cardiograms containing a predetermined number of loops and constituting said sequence of recurring individual spatial closed electrode potential patterns;

said step of transmitting successive measured electrode potentials measured at related scanning moments of time within a predetermined time interval includes the step of selecting a time interval of a duration approximately equal to the duration of a QRS-loop of an individual one of said recurring vector cardiograms; and said step of defining said reference point includes the step of determining the first occurring scanning moment of time which is associated with said maximum positive slope in the QRS-loop of said individual vector cardiogram.

20. The method as defined in claim 19, further including the steps of:

determining the maximum positive spatial slopes of the preselected loops of a predetermined number of individual ones of said time sequence of recurring vector cardiograms;

determining an average maximum positive spatial slope from the maximum positive spatial slopes determined for each one of the preselected loops of said predetermined number of individual vector cardiograms;

comparing the average maximum positive spatial slope with the individual maximum positive spatial slopes of the preselected loops of said predetermined number of individual vector cardiograms, and, as a result of such comparison, determining upper and lower limiting values and a predetermined acceptable spread of maximum positive spatial slope values; and transferring said upper and lower limiting values of said spread of acceptable maximum positive spatial slope values to said measured data storage.

21. The method as defined in claim 20, further including the steps of:

selecting from said predetermined number of individual vector cardiograms a selected number of individual vector cardiograms, the preselected loops of which have a maximum positive spatial slope value within said predetermined acceptable spread of maximum positive spatial slope values;

determining the first one in the time sequence of said selected number of individual vector cardiograms;

transferring a first sample of electrode potentials measured during a first time interval, which extends from a preselected moment of time preceding said reference point of said preselected loop of the first one of said selected number of individual vector cardiograms to a first moment of time preceding said preselected moment of time, from said measured data storage to a first data storage operatively connected thereto by means of said data and address bus;

supplying addresses associated with said first sample of measured electrode potentials from said measured data storage to a first address counter by means of said data and address bus;

transferring a second sample of electrode potentials measured during a second time interval, which extends from a further preselected moment of time following said reference point of said preselected loop of said first one of said selected number of individual vector cardiograms to a second moment of time following said further preselected moment of time, from said measured data storage to a second data storage by means of said data and address bus; and supplying addresses associated with said second sample of measured electrode potentials from said measured data storage to a second address counter by means of said data and address bus.

22. The method as defined in claim 21, further including the step of:

selecting as said first time interval a time interval extending from a preselected moment of time preceding said reference point by about 20 milliseconds to a first moment of time preceding said reference point by a time period in the range of 60 to 140 milliseconds and including the starting point of said preselected loop of said first one of said selected number of individual vector cardiograms; and selecting as said second time interval a time interval extending from a further preselected moment of time following said reference point by about 20 milliseconds to a second moment of time following said reference point by a time period in the range of 160 to 200 milliseconds and including the end point of said preselected loop of said first one of the selected number of individual vector cardiograms.

23. The method as defined in claim 18, further including the steps of:

controlling the determination of said spatial slope of said preselected loop of said selected individual spatial closed electrode potential pattern by means of a program sequencer operatively connected to said arithmetic logic unit and to said measured data storage by means of a data and address bus.

24. The method as defined in claim 16, further including the steps of:

determining the spatial slopes of the preselected loops of a predetermined number of individual spatial closed electrode potential patterns of said time sequence of individual spatial closed electrode potential patterns;

determining an average spatial slope from the spatial slopes determined for each one of the preselected loops of the predetermined number of said individual spatial closed electrode potential patterns;

comparing the average spatial slope with the individual spatial slopes of the preselected loops of said predetermined number of individual spatial closed electrode potential patterns, and, as a result of such comparison, determining upper and lower limiting values and a predetermined acceptable spread of spatial slope values; and transferring said upper and lower limiting values of said spread of acceptable spatial slope values to said measured data storage.

25. The method as defined in claim 24, further including the steps of:

selecting from said predetermined number of individual spatial closed electrode potential patterns a selected number of individual spatial closed electrode potential patterns, the preselected loops of which have a spatial slope value within said predetermined acceptable spread of spatial slope values;

determining the first one in the time sequence of said selected number of individual spatial closed electrode potential patterns;

transferring a first sample of electrode potentials measured during a first time interval, which extends from the moment of time associated with said reference point of said preselected loop of said first one of said selected number of individual spatial closed electrode potential patterns to a preceding moment of time in the region of the starting point of said preselected loop of said first one of said selected number of individual spatial closed electrode potential patterns, from said measured data storage to a first data storage operatively connected thereto by means of said data and address bus;

supplying addresses associated with said first sample of measured electrode potentials from said measured data storage to a first address counter by means of said data and address bus;

transferring a second sample of electrode potentials measured during a second time interval, which extends from said moment of time associated with said reference point of said preselected loop of said first one of said selected number of individual spatial closed electrode potential patterns to a following moment of time in the region of the end point of said preselected loop of said first one of the selected number of individual spatial closed electrode potential patterns, from said measured data storage to a second data storage by means of said data and address bus; and supplying addresses associated with said second sample of measured electrode potentials from said measured data storage to a second address counter by means of said data and address bus.

26. The method as defined in claim 25, further including the steps of:

storing the measured electrode potential associated with said reference point and the address of said reference point at a null address in said measured data storage;

determining the spatial distances between the first measured electrode potentials stored in said first data storage and the second measured electrode potentials stored in said second data storage;

transmitting each determined spatial distance to an intermediate storage operatively connected to said arithmetic logic unit and supplying the associated addresses to an intermediate address storage;

sequentially comparing by means of a comparator the spatial distances determined between the first measured electrode potentials of said first sample stored in said first data storage and the second measured electrode potentials of said second sample stored in said second data storage;

determining the minimum spatial distance between the first measured electrode potentials of said first sample and the second measured electrode potentials of said second sample;

defining the first measured electrode potential of said first sample and the related address associated with said minimum spatial distance as the starting point of said preselected loop of said first one of the selected number of individual spatial closed electrode potential patterns;

defining the second measured electrode potential of said second sample and the related address associated with said minimum spatial distance as the end point of said preselected loop of said first one of the selected number of individual spatial closed electrode potential patterns; and transmitting said first measured electrode potential and said second measured electrode potential and the related addresses to a null address of said measured data storage.

27. The method as defined in claim 26, further including the steps of:

repeating the steps of determining and transmitting the first and second measured electrode potentials and the related addresses associated with the minimum spatial distance as the starting point and as the end point for the preselected loops of the remaining ones of the selected number of individual spatial closed electrode potential patterns and which preselected loops have a predetermined spatial slope value within said predetermined acceptable spread of predetermined spatial slope values.

28. The method as defined in claim 25, further including the steps of:

storing a maximum measured electrode potential associated with the preselected loop of the first one of said selected individual spatial closed electrode potential pattern at a null address in said measured data storage;

determining the spatial distances between the first measured electrode potentials stored in said first data storage and the second measured electrode potentials stored in said second data storage;

comparing by means of a comparator the spatial distances determined between the first measured electrode potentials of said first sample stored in said first data storage and the second measured electrode potentials of said second sample stored in said second data storage with the maximum measured electrode potential stored in said measured data storage at the null address thereof and storing the smaller one of the two data in said measured data storage at said null address thereof;

sequentially comparing by means of said comparator the spatial distances determined between all of the first measured electrode potentials of said first sample stored in said first data storage and all of the second measured electrode potentials of said second sample stored in said second data storage, with the datum stored in said measured data storage at the null address thereof such that the minimum spatial distance is stored at said null address of said measured data storage as a result of the comparing operation;

defining the first measured electrode potential and the related address associated with said minimum spatial distance as the starting point of the preselected loop of said first one of the selected individual spatial closed electrode potential patterns; and defining the second measured electrode potential and the related address associated with said minimum spatial distance as the end point of the preselected loop of said first one of the selected number of individual spatial closed electrode potential patterns.

29. The method as defined in claim 28 further including the steps of:

repeating the steps of determining the first and second measured electrode potentials and the related addresses associated with the starting point and with the end point of the preselected loops of the remaining ones of the selected number of individual spatial closed electrode potential patterns and which preselected loops have a predetermined spatial slope value within said predetermined acceptable spread of predetermined spatial slope values.

30. An apparatus for recording and processing a signal constituted by measured data which vary in time and space and define a time sequence of recurring individual spatial closed signal patterns, comprising:

a measuring unit containing a predetermined number of sensors for sensing said signal;

a measured data storage;

said measured data storage storing the measured data and their associate addresses and containing a null address storage at which the measured data associated with a starting point and an end point of each said individual spatial closed signal pattern is stored;

an analog-to-digital converter having an input side and an output side;

said analog-to-digital converter being connected on its input side to said measuring unit and being connected on its output side to said measured data storage;

means for determining a slope of each one of said individual spatial closed signal patterns at a preselectable reference point and for transmitting the measured datum and address of said preselected reference point to said measured data storage;

a data and address bus operatively interconnecting said means for determining said preselected reference point and said measured data storage;

a sampling unit;

said sampling unit containing first sampling means for sampling a first sample of measured data and their associated addresses which precede said reference point in each one of said individual spatial closed signal patterns;

said sampling unit further containing second sampling means for sampling a second sample of measured data and their associated addresses which follow said reference point in each one of said individual spatial closed signal patterns;

said first sampling means and said second sampling means being operatively connected to said measured data storage by means of said data and address bus;

means for sequentially determining the spatial distance between the measured data of said first sample and the measured data of said second sample;

comparating means operatively connected to said means for sequentially determining said spatial distances and comparing said spatial distances, in order to determine a minimum spatial distance;

said comparating means being operatively connected to said measured data storage and transferring the measured datum of said first sample which is associated with said minimum spatial distance to said null address of said measured data storage; and a program sequencer operatively connected to said measured data storage, said slope determining means, said sampling unit, and said comparating means and controlling the slope determination, the sampling operation and the comparating operation.

31. The apparatus as defined in claim 30, wherein:
said slope determining means and said comparating means form parts of a common arithmetic logic unit.

32. The apparatus as defined in claim 30, wherein:
said first sampling means comprise a first data storage and a first address storage; and
said second sampling means comprising a second data storage and a second address storage.

33. The apparatus as defined in claim 30, wherein:
said predetermined number of sensors comprises a predetermined number of electrodes arranged in a predetermined spatial configuration at the body of a living being to be investigated; and
said time sequence of recurring individual spatial closed signal patterns constituting a time sequence of recurring individual spatial closed electrode potential patterns of a vector cardiogram.

* * * * *

UNITED STATES PATENT AND TRADEMARK OFFICE
CERTIFICATE OF CORRECTION

PATENT NO. : 4,587,976
DATED : May 13, 1986
INVENTOR(S) : Johann J. Schmid and Werner Thie It is certified that error appears in the above—identified patent and that said Letters Patent is hereby corrected as shown below:

Column 4, line 42, after "to the" delete "example" and insert --example--

Column 5, line 48, delete "1oop" and insert --loop--

Column 10, line 24, after "which" delete "are"

Column 10, line 31, after "for the" delete "spatia1" and insert --spatial--

Column 10, line 43, after "value" delete "L. V" and insert --LV--

Column 11, line 18, after "80" insert --milliseconds and the second time interval 26 extends from a--

Column 11, line 18, delete "preseIcted" and insert --preselected--

Column 14, line 45, after "closed" delete "siqnal" and insert --signal--

Signed and Sealed this

Fourth Day of November, 1986

[SEAL]

Attest:

DONALD J. QUIGG

Attesting Officer  Commissioner of Patents and Trademarks